United States Patent [19]

Ravel et al.

[11] Patent Number: 5,488,866
[45] Date of Patent: Feb. 6, 1996

[54] TIME-INTERLEAVED METHOD FOR EFFICIENT OPERATION OF AN ACOUSTIC WAVE SENSOR ARRAY

[75] Inventors: Mihir K. Ravel; Steven H. Pepper, both of Portland, Oreg.

[73] Assignee: Tektronix, Inc., Wilsonville, Oreg.

[21] Appl. No.: 225,867

[22] Filed: Apr. 11, 1994

[51] Int. Cl.⁶ .................................................. G01N 29/08
[52] U.S. Cl. ......................... 73/579; 73/610; 340/870.13
[58] Field of Search .............................. 73/610, 579, 626, 73/628; 364/507, 508; 340/870.13, 870.14; 367/79, 20

[56] References Cited

U.S. PATENT DOCUMENTS

| | | | |
|---|---|---|---|
| 4,092,629 | 5/1978 | Siems | 340/870.13 |
| 4,092,852 | 6/1978 | Fowler | 340/870.13 |
| 4,312,228 | 1/1982 | Wohitjen | 73/597 |
| 5,058,080 | 10/1991 | Siems | 340/870.14 |

OTHER PUBLICATIONS

"Smart Sensor System for Trace Organophosphorus and Organosulfur Vapor Detection Employing a Temperature–Controlled Array of Surface Acoustic Wave Sensors, Automated Sample Preconcentration, and Pattern Recognition" (Anal. Chem. 1993, 65, 1868–1881) Jay W. Grate, Susan L. Rose—Pehrsson, David L. Venezky, Mark Klusty and Hank Wohltjen.
"Multiple–Frequency SAW Devices for Chemical Sensing and Materials Characterization" (Sensors and Actuators B, 10 (1993) 123–131) Antonio J. Ricco and Stephen J. Martin.
"Thin Aluminum Nitride Film Resonators: Miniaturized High Sensitivity Mass Sensors" (Analytical Chemistry, 1992, 64) Ronald P. O'Toole, Stanley G. Burns, Glenn J. Bastiaans and Marc D. Porter.
"Multicomponent Analysis Using an Array of Piezoelectric Crystal Sensors" (Anal. Chem. 1987, 59 1529–1534) W. Patrick Carey, Kenneth R. Beebe and Bruce R. Kowalski.

*Primary Examiner*—Hezron E. Williams
*Assistant Examiner*—Christine K. Oda
*Attorney, Agent, or Firm*—Francis I. Gray; John Smith-Hill; Boulden G. Griffith

[57] ABSTRACT

A time-interleaved method for efficient operation of an acoustic wave sensor array couples each sensor repetitively and one at a time via a digitally-addressable analog switch, or multiplexer, to a single oscillator driver to form an oscillation circuit. A frequency of oscillation for each acoustic wave sensor is determined. The frequency for each acoustic wave sensor then is converted into a measurement value for the parameter to which each acoustic wave sensor is sensitive.

12 Claims, 1 Drawing Sheet

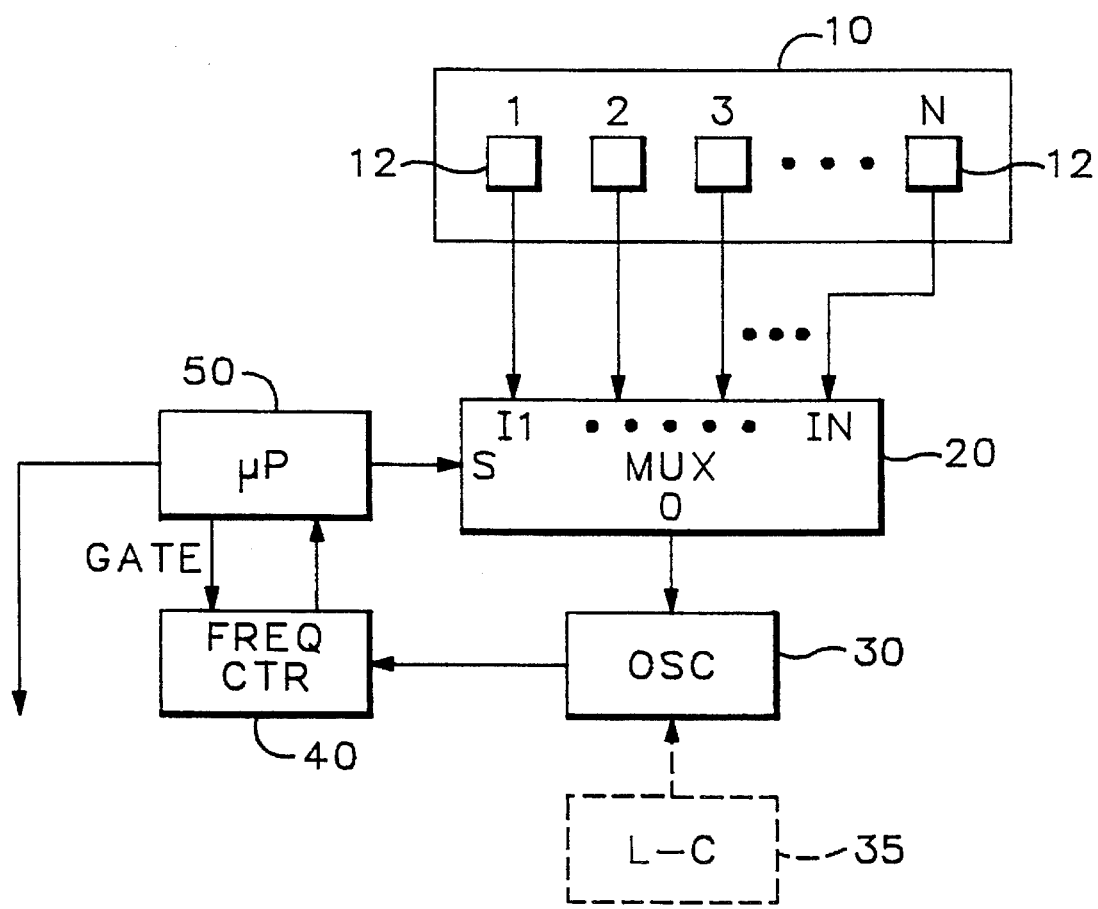

5,488,866

TIME-INTERLEAVED METHOD FOR EFFICIENT OPERATION OF AN ACOUSTIC WAVE SENSOR ARRAY

BACKGROUND OF THE INVENTION

The present invention relates to acoustic wave sensors, and more particularly to a time-interleaved method for efficient operation of an acoustic wave sensor array for detecting parameters of interest, such as chemical concentration, pressure, humidity, temperature and the like.

Acoustic wave devices, such as surface acoustic wave (SAW) devices, thin film resonators, quartz crystal microbalances and the like, may be used as sensors for chemical and physical detection by coating them with materials sensitive to a parameter of interest, as disclosed in U.S. Pat. No. 4,312,228 issued Jan. 26, 1982 to Henry Wohltjen entitled "Methods of Detection with Surface Acoustic Wave and Apparati Therefor" incorporated herein by reference. Interaction of an acoustic wave with the sensitive material causes a change in the propagation characteristics, such as phase and velocity, of the acoustic wave. Operation of the resulting acoustic wave sensor as an oscillator is a method used for measuring these changes in the acoustic wave propagation characteristics.

A multiplicity of parameters may be measured by using an array of acoustic wave sensors in which each sensor of the array is coated with a different material with unique sensitivity properties. Prior systems of acoustic wave sensor arrays, as described in the 1993 article by Jay W. Grate et al in Analytical Chemistry, vol. 65, pgs. 1868–1881, entitled "Smart Sensor System for Trace Organophosphorus and Organosulfur Vapor Detection Employing a Temperature-Controlled Array of Surface Acoustic Wave Sensors, Automated Sample Preconcentration, and Pattern Recognition" incorporated herein by reference, have used a multiplicity of oscillator circuits with each oscillator driver dedicated to its own acoustic wave sensor. Some of the disadvantages of this approach are excessive power consumption due to each oscillator requiring as much as one Watt of power, excessive self-heating of the acoustic wave sensors as significant power may be dissipated in each sensor, inadvertent frequency locking of oscillators due to coupling between oscillators, and large component count and circuit board space for multiple oscillator circuits.

For field use, as opposed to research or laboratory use, it is desirable to have a measurement instrument that may be readily held in one's hand. To accomplish this it is desired to reduce the power consumption and the parts count as well as to prevent frequency locking between oscillators so each acoustic wave sensor in an array responds independently from the others.

SUMMARY OF THE INVENTION

Accordingly the present invention provides a time-interleaved method for efficient operation of an acoustic wave sensor array by providing a single oscillator driver. The oscillator driver is coupled to each acoustic wave sensor in turn via a digitally-addressable analog switch, referred to herein as a multiplexer, to complete an oscillator circuit. The multiplexer addresses each sensor in turn for a short period of time in a repetitive fashion so that each sensor is brought into oscillation one at a time. For N sensors this reduces power dissipation and component count by a factor of N, and also eliminates the possibility of cross-talk between sensors since only one sensor oscillates at any one time.

The objects, advantages and other novel features of the present invention are apparent from the following detailed description when read in conjunction with the appended claim and attached drawing.

BRIEF DESCRIPTION OF THE DRAWING

The FIGURE is a block diagram view of a time-interleaved system for efficient operation of an acoustic wave sensor array according to the present invention.

DESCRIPTION OF THE PREFERRED EMBODIMENT

Referring now to the FIGURE an acoustic wave sensor array 10 has a plurality of acoustic wave sensors 12, each having a coating material sensitive to a different parameter to be measured, such as chemical composition, pressure, humidity, temperature or the like. The outputs from the sensors 12 are input to a digitally-addressable analog switch 20, herein referred to as a multiplexer, which selects one of the inputs in turn as an output. The output of the multiplexer 20 is coupled to an oscillator driver 30 so that the selected sensor 12 completes a resonant circuit with the oscillator driver. The resulting oscillator signal is taken from the oscillator driver 30 and input to a frequency counter 40. The frequency counter 40 measures the frequency of the oscillator signal from the oscillator driver in response to a gate pulse from a microprocessor 50. At the conclusion of the gate pulse the frequency measured by the frequency counter 40 is transferred to the microprocessor 50 for processing to provide a measure of the parameter to which the selected sensor 12 is sensitive. The microprocessor 50 also provides a select command in the form of a digital address to the multiplexer 20 to determine which sensor 12 is coupled to the oscillator driver 30 at any one time.

The microprocessor 50 has stored in its memory a nominal frequency for each sensor/oscillator driver combination corresponding to a nominal calibration value, such as no presence for a chemical concentration or one atmosphere for a pressure, etc. Deviations from the nominal frequency are interpreted by the microprocessor 50 as a measure of the particular parameter based upon a calibration curve, also contained in the microprocessor memory. The microprocessor 50 outputs the measured values for each sensor 12 in a suitable form, such as alphanumeric, graphic or the like, for display.

For example each sensor 12 may be coated for sensitivity to a different unique chemical pollutant in a fluid environment. The microprocessor 50 may address each sensor 12 via the multiplexer 20 for 10 milliseconds at a time, which allows N oscillators to be addressed at N* 10 millisecond intervals. For N=10 the intervals are 100 milliseconds. The requirements for the two intervals, TM (time for measurement of an individual sensor 12) and TT (total time for addressing N sensors 12 where TT=N*TM) are as follow:

1. TM should be longer than a time TS required for an oscillator formed by the selected sensor 12 and the oscillator driver 30 to start up and stabilize. The time TS is on the order of the oscillator Q multiplied by the oscillation period. Since most acoustic wave devices are high Q (100–10,000) devices with oscillation frequencies of 10 MHz–1 GHz (periods of 100–1 nanoseconds), the time TS is on the order of 100 nanoseconds to 100 microseconds. With the time TM of 10 milliseconds there is sufficient measurement time for measurement of the oscillator frequency after the time TS. The oscillator driver 30 may include a means for energy storage in the form of an L-C tank circuit 35 to maintain an oscillation signal during resonator switching. This shortens the start-up time of the oscillator driver 30 since the oscillator signal does not have to build up from noise.

2. TT should be significantly less than the thermal time constants, TH, of the acoustic wave sensors 12 and their housing. Since stable operation of the acoustic wave sensors 12 typically requires temperature control of the sensors, uniform heating of the sensors is preferred. If TH is 5 seconds and TT is 100 milliseconds, then each sensor 12 is heated every 100 milliseconds and maintains an approximately constant temperature since there is little cooling of the sensor during the 100 milliseconds. In this time averaged fashion the entire sensor array 10 maintains an approximately constant and uniform power dissipation.

The sensors 12 may be repetitively coupled by the microprocessor 50 to the oscillator driver 30 via the multiplexer 20 in an order that is other than linearly sequential to optimize heat distribution patterns. The gate signal from the microprocessor 50 may also serve to connect/disconnect the frequency counter 40 used for detecting frequency shifts if the counter is disturbed by the transients associated with switching from sensor to sensor, as discussed above. The result is a reduction by a factor of N in component count and power, which is important in the implementation of small, portable instrumentation where there are significant restraints on size, weight and power requirements.

Thus the present invention provides a time-interleaved method for efficient operation of an acoustic wave sensor array by using a single oscillator driver and coupling each sensor of the array in turn via a digitally-addressable analog switch, or multiplexer, to the oscillator driver. The frequency generated by each sensor in turn is determined by a frequency counter and interpreted by a microprocessor as a measurement of the parameter to which the selected sensor is sensitive.

What is claimed is:

1. A system for measuring a plurality of parameters using a plurality of acoustic wave sensors associated with the parameters respectively, wherein the parameters are aspects of the acoustic wave sensor's environment chosen from the set of chemical aspects and physical aspects such that a change in one of said parameters causes a change in acoustic propagation properties of the associated acoustic wave sensor, the system comprising:

an oscillator driver having an input and an output;

means for repetitively selecting each of the acoustic wave sensors for coupling one at a time to the input of the oscillator driver to complete an oscillator circuit and produce an oscillator signal at the output of the oscillator driver for each of the acoustic wave sensors;

means for determining frequency of the oscillator signal for each of the acoustic wave sensors; and means for converting the frequency to a measurement value for display for each of the acoustic wave sensors.

2. The system as recited in claim 1 wherein the selecting means comprises a digitally-addressable analog switch having N inputs, where N is the number of acoustic wave sensors, and one output, each of the acoustic wave sensors being coupled separately to one of the N inputs and the oscillator driver input being coupled to the one output.

3. The system as recited in claim 1 wherein the determining means comprises a frequency counter having an input coupled to the output of the oscillator driver and having an output coupled to the converting means, the frequency counter measuring the frequency of the oscillator signal within a specified measurement interval for each of the acoustic wave sensors.

4. The system as recited in claim 3 wherein the frequency counter includes a gate input coupled to the converting means for receiving a gate signal for turning on and off the counter so that the counting for each of the acoustic wave sensor occurs within the specified measurement interval after transients have settled.

5. The system as recited in claim 1 wherein the converting means comprises a microprocessor having an input for receiving the frequency from the determining means, having an output for providing the measurement value for display, and having a select output coupled to the selecting means for determining a sequence in which the acoustic wave sensors are repetitively selected by the selecting means.

6. The system as recited in claim 5 wherein the microprocessor has a gate output coupled to the determining means for turning on and off the determining means so that the frequency for each of the acoustic wave sensors is determined within a measurement interval after transients have settled.

7. A method of measuring a plurality of parameters using a plurality of acoustic wave sensors associated with the parameters respectively, wherein the parameters are aspects of the acoustic wave sensor's environment chosen from the set of chemical aspects and physical aspects such that a change in one of said parameters causes a change in acoustic propagation properties of the associated acoustic wave sensor, the method comprising the steps of:

repetitively selecting each of the acoustic wave sensors one at a time for coupling to an oscillator driver to complete an oscillation circuit;

determining frequency of oscillation for the oscillation circuit for each of the sensors; and convening the frequency for each of the acoustic wave sensors to a measurement value for display that represents the parameter with which the acoustic wave sensor is associated.

8. A method of measuring N parameters, where N is an integer greater than two, using N acoustic wave sensors associated with the parameters respectively, wherein the parameters are aspects of the acoustic wave sensor's environment chosen from the set of chemical aspects and physical aspects such that a change in one of said parameters causes a change in acoustic propagation properties of the associated acoustic wave sensor, the method comprising the steps of:

(a) selecting a first of the N acoustic wave sensors, (b) coupling the selected acoustic wave sensor to an oscillator driver to complete an oscillation circuit, whereby the oscillation circuit oscillates at a frequency that depends on the acoustic propagation properties of the selected acoustic wave sensor, (c) determining the frequency of oscillation of the oscillation circuit, (d) converting the frequency of oscillation of the oscillation circuit to a measurement value that represents the parameter with which the selected acoustic wave sensor is associated, (e) selecting one of the N acoustic wave sensors that has not been selected since the first acoustic wave sensor was selected, (f) repeating steps (b)–(d), (g) repeating steps (e) and (f) N-2 times.

9. A method according to claim 8, wherein the method comprises a preliminary step of storing a nominal frequency for each of the acoustic wave sensor, and step (d) comprises providing a measurement value dependent on deviation of the frequency of oscillation of the oscillation circuit from the stored nominal frequency.

10. A method according to claim 9, wherein step (d) further comprises outputting the measurement value in a for display.

11. A method according to claim 8, wherein step (d) further comprises outputting the measurement value for display.

12. A method according to claim 8, wherein step (d) comprises providing a measurement value dependent on deviation of the frequency of oscillation of the oscillation circuit from a nominal frequency.

* * * * *